US00PP23547P2

(12) United States Plant Patent
Kordes

(10) Patent No.: US PP23,547 P2
(45) Date of Patent: Apr. 23, 2013

(54) SHRUB ROSE PLANT NAMED 'KORJUWKO'

(50) Latin Name: *Rosa hybrida*
Varietal Denomination: KORjuwko

(75) Inventor: Tim-Hermann Kordes, Klein Offenseth-Sparrieshoop (DE)

(73) Assignee: W. Kordes Söhne Rosenschulen GmbH & Co KG, Offenseth-Sparrleshoop (DE)

( * ) Notice: Subject to any disclaimer, the term of this patent is extended or adjusted under 35 U.S.C. 154(b) by 0 days.

(21) Appl. No.: 13/135,845

(22) Filed: Jul. 14, 2011

(51) Int. Cl.
*A01H 5/00* (2006.01)

(52) U.S. Cl. ..... Plt./108

(58) Field of Classification Search ..... Plt./108
See application file for complete search history.

*Primary Examiner* — Kent L Bell

(57) ABSTRACT

A new and distinct shrub rose variety with long lasting, novel velvet red flowers, and attractive foliage with excellent disease resistance. It exhibits upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORjuwko'.

The new variety of rose plant of the present invention originated from a controlled crossing in a breeding program of two distinct parents during the summer of 2001. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORjuwko'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an 'un-named seedling', by the following combination of characteristics:

1. The flower color of 'KORjuwko' is velvet red while the flower color of the seed parent is dark red.
2. The foliage of 'KORjuwko' is glossy while the foliage of the seed parent is very glossy.

The new rose plant may be distinguished from its pollen parent, an 'un-named seedling' by the following combination of characteristics:

1. The flower shape of 'KORjuwko' is roundish while the flower shape of the pollen parent is cupped.
2. The petal count of 'KORjuwko' is semi double while the petal count of the pollen parent is single.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORjuwko' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORjuwko' was selected in May, 2002 from the seedling beds to be asexually propagated for further evaluation. The first asexual propagation of 'KORjuwko' was done by budding to seedling understocks in July, 2002 at the inventor's nursery in Offenseth-Sparrieshoop, Germany.

This initial and other subsequent propagations conducted in controlled environments demonstrate that 'KORjuwko' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORjuwko'.

DETAILED BOTANICAL DESCRIPTION

The following is a description of 'KORjuwko', as observed growing in June, 2011 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORcasima', a rose variety from the same inventor described and illustrated in U.S. Plant Pat. No. 20,732 and issued on Feb. 9, 2010 are compared to 'KORjuwko' in Chart 1.

CHART 1

| Characteristic | 'KORjuwko' | 'KORcasima' |
|---|---|---|
| Petal count: | Semi double (about 16). | Very double (about 70-80). |
| Flower bloom duration: | On the plant, 3-4 days. | On the plant, 6-7 days. |
| Pistils: | Approx. 12 present. | Approx. 35-40 present. |

Parents:

*Seed parent.*—An 'un-named seedling'.

*Pollen parent.*—An 'un-named seedling'.

Classification:

*Botanical classification.—Rosa hybrida,* 'KORjuwko'.

*Commercial classification.*—Shrub rose.

FLOWER AND FLOWER BUD

Blooming habit: Continuous.

Flower bud:

*Size.*—Upon opening, 15 mm in length from base of receptacle to end of bud and 12 mm diameter at its widest point.

*Bud form.*—Long. Pointed ovoid.

*Bud color.*—As sepals first unfold, bud color is between Greyed-Purple Group 187A and Grayed-Purple Group 187B. When ¼ open, the upper surface of petals is Red Group 53A, and the lower surface is Red Group 46A. Guard Petals: No color change.

*Sepals.*—Color: Upper surface Yellow-Green Group 146C. Lower surface Yellow-Green Group 146B. Intonations of Greyed-Purple Group 185B in the center of the sepals on both upper and lower surfaces. Size: Average 25-40 mm long×5-6 mm wide. Base: Flat at union with peduncle. Shape: Strong foliaceous appendages on two to three of the five sepals. Apex: Variable. Typically, 3-4 are apiculate with the remaining sepals being cirrose. Quantity: Five. Surface texture: Upper side: Pubescent. Lower surface: Rough with stipitate glands. Margins: Stipitate glands on margins as well as on foliaceous appendages.

Receptacle:

*Surface.*—Generally smooth with occasional stipitate glands.

*Color.*—Yellow-Green Group 146B. Anthocyanin is Greyed-Purple Group 183B.

*Shape.*—Urn-shaped.

*Size.*—8 mm (h)×6-7 mm (w).

Peduncle:

*Surface.*—With stipitate glands.

*Length.*—35 to 40 mm average length.

*Diameter.*—1 to 2 mm average diameter.

*Color.*—Yellow-Green Group 146D.

*Strength.*—Strong.

*Borne.*—Multiple flower buds per stem, generally 1-4.

Flower bloom:

*Fragrance.*—Light. Fruity.

*Duration.*—On the plant 3-4 days. As a cut flower, 3-4 days. Senesced petals drop away cleanly.

*Size.*—Medium. When open, the average flower diameter is 65-75 mm and the average flower height is 35-40 mm.

*Form.*—Shape of flower when viewed from the side: Upon opening, upper part: Flat. Upon opening, lower part: Concave. Open flower, upper part: Flat. Open flower, lower part: Concave.

Color:

*Upon opening, petals.*—Outermost petals: Outer Side: Red Group 53B. Inner Side: Red Group 45B. Innermost petals: Outer Side: Red Group 54C. Inner Side: Red Group 46B.

*Upon opening, basal petal spots.*—Basal petal spot, outermost petals: Outer Side: White Group 155B. Inner Side: White Group 155B. Basal petal spot, innermost petals: Outer Side: Green-Yellow Group 1D. Inner Side: Green-Yellow Group 1D.

*After opening, petals.*—Outermost petals: Outer Side: Red Group 53B. Inner Side: Red Group 53B. Innermost petals: Outer Side: Red Group 53C. Inner Side: Red Group 53B.

*After opening, basal petal spots.*—Basal petal spot, outermost petals: Outer Side: White Group 155B. Inner Side: White Group 155B. Basal petal spot, innermost petals: Outer Side: White Group 155D. Inner Side: White Group 155B.

General tonality: On open flower Red Group 53B. No change in the general tonality at the end of the 4th day. Thereafter, Red Group 53C.

Petals:

*Petal count.*—Semi double. Average Range: About 16 petals under normal conditions.

*Petal reflex.*—Petals reflex slightly.

*Petal edge.*—Rounded. The center of the petal edge is indented.

*Petal shape.*—Ovate. Apex shape is obtuse. Shape of base is deltoid.

*Petal size.*—30-35 mm (l)×30-35 mm (w).

*Thickness.*—Average.

*Petal arrangement.*—Not formal.

Petaloids: Usually a few present.

*Petaloid count.*—Average of 0-4 per flower.

*Petaloid size.*—Petaloids are 3-4 mm long and 1-2 mm wide.

*Petaloid color.*—Color of inner side is between Red Group 53B and Red Group 53C. Color of outer side is Red Group 53C.

*Petaloid texture.*—Smooth.

*Margins.*—Indented.

*Petaloid shape.*—Overall: Deltoid to obtuse. Apex: Obtuse. Base: Deltoid.

Reproductive organs:

*Pistils.*—Approximately 12 present. Stigmas: Location: Slightly inferior in position to anthers. Color: Yellow Group 11C. Styles: Length: 3 mm long, on average. Color: Yellow-Green Group 144B at base with intonations of Red Group 47C at upper portion.

*Stamens.*—Approximately 35 on average and regularly arranged. Anthers: Size: About 1 mm long. Pollen: Generally present. Color: Yellow-Orange Group 22A. Filaments: Color: Green-Yellow Group 1B at base with upper portions Yellow-Orange Group 22A. Length: 4-5 mm on average.

THE PLANT

Plant growth: Moderate upright habit. When grown as a budded field grown plant, the average plant height is 80 cm and the average plant width is 60 cm.

Blooming: Floriferous.

Stems:

*Stem color*.—Young wood: Yellow Group 144B. Older wood: Yellow-Green Group 146B.

*Stem surface*.—Young wood: Smooth. Older wood: Smooth to rough.

Prickles: Present.

*Incidence*.—On average, 5-6 prickles per 10 cm of stem.

*Size*.—Average length: 7 mm.

*Color*.—Immature prickles: Green Group 138C with intonations of Greyed-Purple Group 185D. Mature prickles: Brown Group N200B. Color at point of attachment to stem is Greyed-Brown Group 199D.

*Shape*.—Concave.

*Anthocyanin*.—None observed.

Leaves and leaflets: Normally 5 leaflets on normal leaves in middle of the stem.

*Venation pattern*.—Pyramidal net pattern.

*Leaf size*.—120 mm (l)×100 mm (w).

*Abundance*.—Average.

*Texture*.—Thick. Upper side of leaflet: Glossy on upper side, smooth. Under side of leaflet: Matte, rough.

*Color, mature foliage*.—Upper Leaf Surface: Yellow-Green Group 146A. Lower Leaf Surface: Yellow-Green Group 148B.

*Color, juvenile foliage*.—Upper Leaf Surface: Yellow-Green Group 146A. Lower Leaf Surface: Yellow-Green Group 146C.

*Anthocyanin intonation*.—Present. Intonations present on lower side of immature foliage on margins. Color Greyed-Purple Group 183B.

Stipules:

*Average size*.—Main body of stipule 15 mm (l)×7 mm (w).

*Stipule color*.—Yellow-Green Group 144A.

*Anthocyanin*.—The upper side is Greyed-Red Group 181C.

*Texture*.—Rough with stipitate glands present. Very limited pubescence.

*Shape*.—The main body is linear in shape. The apical end with moderately long straight points that usually turn out at an angle. The proximal end is flat at the point of attachment to the stem.

*Margin*.—Rough with numerous stipitate glands.

Petiole:

*Length*.—15 mm on average.

*Diameter*.—1.5 mm on average.

*Petiole color*.—Yellow-Green Group 146C.

*Underneath*.—Smooth with few to no prickles.

*Margins*.—Stipitate glands.

*Anthocyanin*.—Greyed-Red Group 181D.

Petiole rachis:

*Length*.—20 mm.

*Diameter*.—1.5 mm.

*Color*.—Yellow-Green Group 146D.

*Underneath*.—Generally smooth. Most commonly with few to no prickles.

*Margins*.—With stipitate glands.

*Anthocyanin*.—On upper side and at the point of leaflet attachment. Between Greyed-Red Group 181C and Greyed-Red Group 181D.

*Prickles*.—A few small prickles underneath.

Leaflets:

*Size*.—Average size of the terminal leaflet is 60 mm (l)×38 mm (w).

*Shape*.—Entire: Ovate. Base: Acute. Apex: Ovate.

*Margins*.—Finely serrated.

*Surface*.—Upper: Glossy. Lower: Matte.

*Texture*.—Leathery.

*Arrangement*.—Odd Pinnate.

Hips/seed formation: None observed.

Winter hardiness: To date, the variety has been grown successfully in Zone 5.

Disease resistance: Excellent resistance to Powdery mildew (*Sphaerotheca pannosa*), blackspot (*Diplocarpon rosae*), and rust (*Phragmidium* sp.) diseases under normal growing conditions.

I claim:

1. A new and distinct variety of rose plant, as described and illustrated herein.

* * * * *

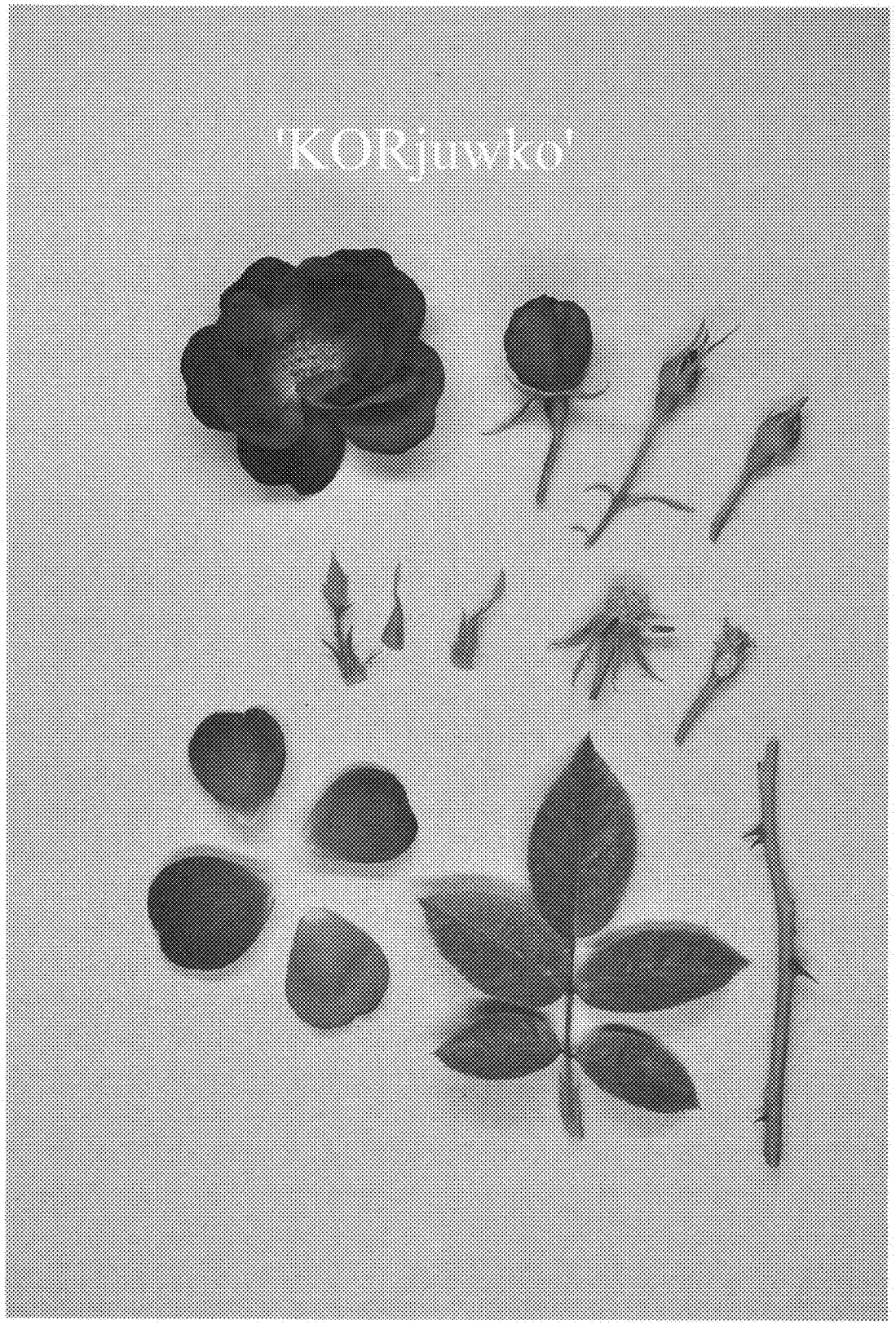
'KORjuwko'